US008470590B2

(12) United States Patent
Adrien et al.

(10) Patent No.: US 8,470,590 B2
(45) Date of Patent: Jun. 25, 2013

(54) MULTIWELL PLATE DEVICE

(75) Inventors: Chris Adrien, Plaistow, NH (US); John C. Bart, Waunakee, WI (US); James Clements, Brentwood, NH (US); David Moore, Dover, NH (US); Bryce P. Nelson, Madison, WI (US)

(73) Assignee: Erie Scientific Company, Portsmouth, NH (US)

( * ) Notice: Subject to any disclaimer, the term of this patent is extended or adjusted under 35 U.S.C. 154(b) by 610 days.

(21) Appl. No.: 12/120,591

(22) Filed: May 14, 2008

(65) Prior Publication Data

US 2008/0287307 A1 Nov. 20, 2008

Related U.S. Application Data

(60) Provisional application No. 60/930,121, filed on May 14, 2007, provisional application No. 60/963,585, filed on Aug. 6, 2007.

(51) Int. Cl.
*C12M 1/22* (2006.01)

(52) U.S. Cl.
USPC ...... 435/305.2; 422/942; 422/500; 435/305.1

(58) Field of Classification Search
USPC ................... 422/102, 942, 500; 435/6, 305.1, 435/305.2
See application file for complete search history.

(56) References Cited

U.S. PATENT DOCUMENTS 6,018,388 A * 1/2000 Nawracala et al. ........... 356/246
6,669,911 B1 * 12/2003 Swanson ....................... 422/102
7,063,979 B2 6/2006 MacBeath et al.
2003/0032046 A1 2/2003 Duffy et al.
2004/0022677 A1 2/2004 Wohlstadter et al.
2005/0135974 A1 6/2005 Harvey et al.
2005/0277145 A1 * 12/2005 Haines et al. ..................... 435/6
2006/0029524 A1 2/2006 Carter et al.

FOREIGN PATENT DOCUMENTS

DE 198 06 681 A1 8/1999
EP 1 652 580 A1 5/2006
JP 9-281106 A 10/1997

OTHER PUBLICATIONS

International Searching Authority/US, International Search Report and Written Opinion of the International Searching Authority, International Application No. PCT/US2008/06170, mailed Aug. 15, 2008 (11 pages).

(Continued)

*Primary Examiner* — Michael Marcheschi
*Assistant Examiner* — Jonathan Hurst
(74) *Attorney, Agent, or Firm* — Wood, Herron & Evans, LLP

(57) ABSTRACT

A multiwell plate device is provided having a frame, a substantially flat substrate and a multiwell structure supported by the substrate. The multiwell structure includes multiple bottomless wells formed therein. The substrate is supported by the frame and may be processed by an automated arrayer or instrument that is used to print or spot arrays in a pattern on a reaction surface of the substrate. Thereafter, the multiwell structure may be engaged with the substrate and the multiwell structure and substrate may be engaged with the frame in an upright orientation. For scanning or other analysis, the multiwell structure and substrate may be disengaged from the frame, inverted 180°, and then reengaged with the frame in the inverted orientation.

29 Claims, 8 Drawing Sheets

OTHER PUBLICATIONS

American National Standards Institute, Society for Biomolecular Sciences for Microplates, Footprint Dimensions, ANSI/SBS Jan. 2004, 8 pages.

American National Standards Institute, Society for Biomolecular Sciences for Microplates, Height Dimensions, ANSI/SBS Feb. 2004, 9 pages.

American National Standards Institute, Society for Biomolecular Sciences for Microplates, Bottom Outside Flange Dimensions, ANSI/SBS Mar. 2004, 10 pages.

American National Standards Institute, Society for Biomolecular Sciences for Microplates, Well Positions, ANSI/SBS Apr. 2004, 13 pages.

European Patent Office, Supplementary European Search Report, Application No. EP08754458.1, date of completion of search is Jun. 29, 2010 (5 pages).

European Patent Office, Examination Report, Application No. 08 754 458.1, dated Oct. 1, 2012 (5 pages).

* cited by examiner

MULTIWELL PLATE DEVICE

The present application claims the filing benefit of U.S. Provisional Ser. No. 60/930,121, filed May 14, 2007, and U.S. Provisional Ser. No. 60/963,585, filed Aug. 6, 2007, the disclosures of which are hereby incorporated herein by reference in their entirety.

FIELD OF THE INVENTION

This invention relates generally to a multiwell plate device and the method for scanning a reaction surface from above and/or below.

BACKGROUND OF THE INVENTION

Multiwell plate devices serve a broad spectrum of laboratory uses. Most applications involve attachment or immobilization of biological materials including, without limitation, biomolecules such as polypeptides and nucleic acids, cells, tissues or fragments biological material, to a surface within the wells (sidewall and/or bottom surface) and the performance of one or more reactions followed by some sort of quantitative and/or qualitative analytical process.

Robotic instruments have been developed for performing automated processing of multiwell plates. Such automated processes include, without limitation, deposition of biological materials (spotting, printing, etc.), addition or removal of reagents, washing, scanning and analysis. The capability of such automated instruments is typically limited to processing plates with "standard" dimensions as established by the Society of Biomolecular Sciences (SBS Standards). Thus, the "footprint" for most multiwell plates is approximately 85 mm×125 mm with wells located in a standardized format depending upon the total number of wells. The American National Standards Institute (ANSI) has published the SBS Standards for microplates as: "Footprint Dimensions" (ANSI/SBS 1-2004), "Height Dimensions" (ANSI/SBS 2-2004), "Bottom Outside Flange Dimensions" (ANSI/SBS 3-2004) and "Well Postions" (ANSI/SBS 4-2004). All of these ANSI/SBS publications are incorporated herein by reference.

Although a standard structure for multiwell plates has facilitated automatic robotic processing, at the same time the structure presents a challenge with regards to certain types of procedures, particularly as the number of wells grows beyond 96. For example, spotting or printing of a microarray on the bottom surface of a well using automatic/robotic liquid handling systems or "arrayers" requires the pin or stylus or other printing/spotting means to move significantly up and down as it arrays one well and moves to the next to print or spot another array. Such movement increases processing time and increases the risk of damage to printing pins or stylus from unwanted collision with plate features above the surface to be printed or arrayed. Therefore, a need exists for a multiwell plate device more conducive to rapid processing.

Moreover, analysis of reactions occurring in the wells of a multiwell plate presents a challenge. Often, the analysis is accomplished by detecting or measuring a change in the material attached to the bottom surface of the wells (substrate) rather than a change in a fluid reaction mixture contained within the wells, as is the case for ELISA-type assays.

Optical detection is the most commonly utilized method to detect changes in surface-localized reactions, particularly with regards to arrays representing multiple different reactions. For surface-localized reactions, the focal plane for proper measurement of the reaction is often limited to a very small range of depths, typically a range of no more than about 5 mm. Analysis, whether done via automated scanning or microscopy or other means, can be performed by directing a light or energy source from above the reaction surface of the substrate or from below (through the substrate) and focusing an optic that captures the detectable signal from above or below the reaction surface. In some cases, for example when certain types of coated substrates and/or mixtures of detection agents are used, analysis from both above and below the reaction surface is useful in order to glean optimal data. However, the design of a standard multi-well plate complicates efforts to analyze results from both above and below the reaction surface. Most automatic scanners/analyzers can scan from only above or below the reaction surface but not both. Because of the dimensions of a standard multiwell plate, the focal plane of the reaction surface (bottom surface of the wells) when the plate is upright is significantly different from the focal plane when the plate is turned over. One prior art solution has been to use two separate analysis systems wherein one is capable of scanning from above the reaction surface and the other from below. Such an approach is expensive and time-consuming. Alternatively, another solution has been use of a multiwell plate device comprising separate pieces assembled to form the plate including a substrate that is detachable from the multiwell plate structure to eliminate physical interference by the plate structure with the focal plane of the reaction surface.

U.S. patent application Ser. No. 10/739,784 to Harvey et al., incorporated herein by reference, teaches the use of 1-4 glass microscope slides placed into a frame-like holder having standard multiwell plate dimensions. The slides are spotted or printed prior to placement in the holder. Once in place in the holder, each slide is topped in a releasable manner with a separate multiwell chamber plate having bottomless wells such that the printed glass slide forms a bottom surface for the chamber plate. Finally a retention means is used to retain the slides in the holder. After processing, the chamber plates and slides are removed from the holder and separated, and each slide is analyzed. Thus, the frame-like holder is used only during the reaction phase of the process; the steps of printing arrays and analyzing results are performed on each individual slide while separated from the holder.

U.S. patent application Ser. No. 11/134,449 to Haines et al., incorporated herein by reference, teaches a device comprising a substrate with a functional coating and biomolecules attached thereto. The substrate is reversibly attached to a superstructure containing multiple openings (multiwell structure). A frame-like tray holds the substrate and serves as an alignment jig for the superstructure. After processing, the system is completely disassembled to remove the substrate for analysis. Thus, the assembled device is used during the reaction phase of the procedure and, optionally, during the step of printing arrays, but it is disassembled for analysis.

U.S. Pat. No. 7,063,979 to MacBeth et al., incorporated herein by reference, teaches a microtiter-microarray device comprising a bottomless multiwell plate structure, one or more substrates having predeposited microarrays, and one or more gaskets for sealing the substrates to the multi-well plate structure. The seal must be fluid-tight but may be either reversible or irreversible. The patent teaches use of a first aligning device to align the gasket and plate structure for attachment purposes and a second aligning device for attachment of the substrates bearing predeposited microarrays. A separate device is used to remove the substrate after processing for analysis via conventional slide scanner. Alternatively, the substrate can remain attached to the gasket and plate structure for analysis via plate scanner, for example, Tecan LS-200 scanner (Tecan, Durham, N.C.). Thus, the reaction surface in a fully assembled multiwell plate device falls within a particular focal plane when the plate is upright and a significantly different focal plane when turned over. As described in U.S. Pat. No. 7,063,979, to scan the reaction surface from the opposite side with a plate scanner, the substrate must be detached and turned over 180°.

A detachable substrate presents a challenge because it must be attached to the plate structure in such a way as to be fluid-tight during the reaction phase of processing and yet removable without a level of force that could break or otherwise damage the substrate and without leaving adhesive or other material that might interfere with analysis. A need exists for a multiwell plate device wherein the reaction surface can be scanned from above or below while maintained within the detectable focal plane of a scanning device without requiring detachment of the substrate from the multiwell plate structure.

SUMMARY OF THE INVENTION

The present invention overcomes the foregoing and other shortcomings and drawbacks of multiwell plate devices heretofore known. While the invention will be described in connection with certain embodiments, it will be understood that the invention is not limited to these embodiments. On the contrary, the invention includes all alternatives, modifications and equivalents as may be included within the spirit and scope of the present invention.

In accordance with one embodiment of the present invention, a multiwell plate device is provided having a frame, a substantially flat substrate including a reaction surface and an opposite bottom surface, and a multiwell structure supported by the substrate. The multiwell structure has multiple bottomless wells formed therein and may be engaged with the reaction surface of the substrate using an adhesive layer. In one embodiment, the frame includes a top surface and defines an opening therethrough. A substrate engaging member, such as a ledge or projection by way of example, is disposed adjacent at least a portion of the opening and has a top surface and an opposite bottom surface.

During use of the multiwell plate device, the substrate may be first placed on the substrate engaging member with the substrate contained by the opening in the frame. In one embodiment, the reaction surface of the substrate is substantially flush with a top surface of the frame so that the reaction surface of the substrate may be manually processed or processed in an automated manner by an arrayer or other instrument that is used to print or spot arrays in a pattern that matches the SBS Standard pattern of wells, or in any other desired pattern.

After the substrate has been printed or spotted or otherwise processed, the multiwell structure is attached to the reaction surface of the substrate while the substrate is retained on the frame. After the multiwell structure and substrate are attached, they are lifted from the frame and the multiwell structure is then at least partially inserted through the opening from beneath the frame with the reaction surface of the substrate engaging the bottom surface of the substrate engaging member. In this configuration, the multiwell plate device is ready for conventional use.

In accordance with one aspect of the present invention, the multiwell plate device is reconfigurable for scanning or other analysis. In particular, the multiwell structure and attached substrate may be removed from the frame through application of a manual force to the multiwell structure. Following disengagement from the frame, the multiwell structure and substrate may then be inverted 180° so that the open ends of the wells are now facing down with the multiwell structure located beneath the substrate. In this inverted orientation, the multiwell structure may be least partially inserted through the opening from above the frame so that the reaction surface of the substrate now engages the top surface of the substrate engaging member.

The frame and multiwell structure may have cooperating alignment structures to assist in aligning the multiwell structure relative to the frame while the multiwell structure is at least partially inserted through the opening from above and beneath the frame.

In one embodiment, the bottom surface of the substrate is generally flush with the top surface of the frame when the multiwell plate and substrate are inverted and engaged with the frame in the inverted orientation. The invertible configuration of the multiwell structure and substrate relative to the frame allows the reaction surface of the substrate to be scanned from both above or below while being maintained within the detectable focal plane of a scanning device without requiring detachment of the substrate from the multiwell structure.

According to another aspect of the present invention, a multiwell plate device is provided having a frame defining an opening therethrough, a substantially flat substrate including a reaction surface and an opposite bottom surface, a multiwell structure supported by the substrate, and at least one projection extending upwardly from the frame. The multiwell structure has multiple bottomless wells formed therein and may be engaged with the reaction surface of the substrate using an adhesive layer.

A substrate receiving surface is disposed adjacent at least a portion of the opening and the at least one projection is positioned outwardly of the substrate receiving surface. The multiwell structure has a pocket formed on a lower side thereof for receiving the substrate therein with the reaction surface of the substrate engaging the multiwell structure. The multiwell structure also includes at least one recess formed on an upper side thereof.

During use of the multiwell plate device according to this embodiment, the substrate is placed on the substrate receiving surface and the substrate may then be manually processed or processed in an automated manner by an arrayer or other instrument that is used to print or spot arrays in a desired pattern on the reaction surface of the substrate. Thereafter, the multiwell structure is engaged with the reaction surface of the substrate by applying downward pressure to the multiwell structure while the substrate is retained on the frame. In this upright orientation of the multiwell structure and substrate, the bottom surface of the substrate engages the substrate receiving surface with the substrate received within the pocket. In this configuration, the multiwell plate device is ready for conventional use.

In accordance with another aspect of the present invention, the multiwell plate device is reconfigurable for scanning or other analysis. In particular, the multiwell structure and attached substrate may be removed from the frame through application of a manual force to the multiwell structure and substrate. Following disengagement from the frame, the multiwell structure and substrate may then be inverted 180° so that the open ends of the wells are now facing down with the multiwell structure located beneath the substrate. In this inverted orientation, the multiwell structure may be reengaged with the frame with the least one projection received in the at least one recess formed on the upper side of the multiwell structure.

The invertible configuration of the multiwell structure and substrate relative to the frame in this embodiment allows the reaction surface of the substrate to be scanned from both above or below while being maintained within the detectable focal plane of a scanning device without requiring detachment of the substrate from the multiwell structure.

The above and other objects and advantages of the present invention shall be made apparent from the accompanying drawings and the description thereof.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

DETAILED DESCRIPTION OF THE PREFERRED EMBODIMENT

The present invention, in one aspect, is a multiwell plate device 10 (see FIG. 8) comprising at least three components: i) a substantially flat substrate 12, ii) a bottomless multiwell structure 14 and a frame 16. In another aspect, the invention is a method for scanning a reaction surface from above and/or below.

Figure 1:
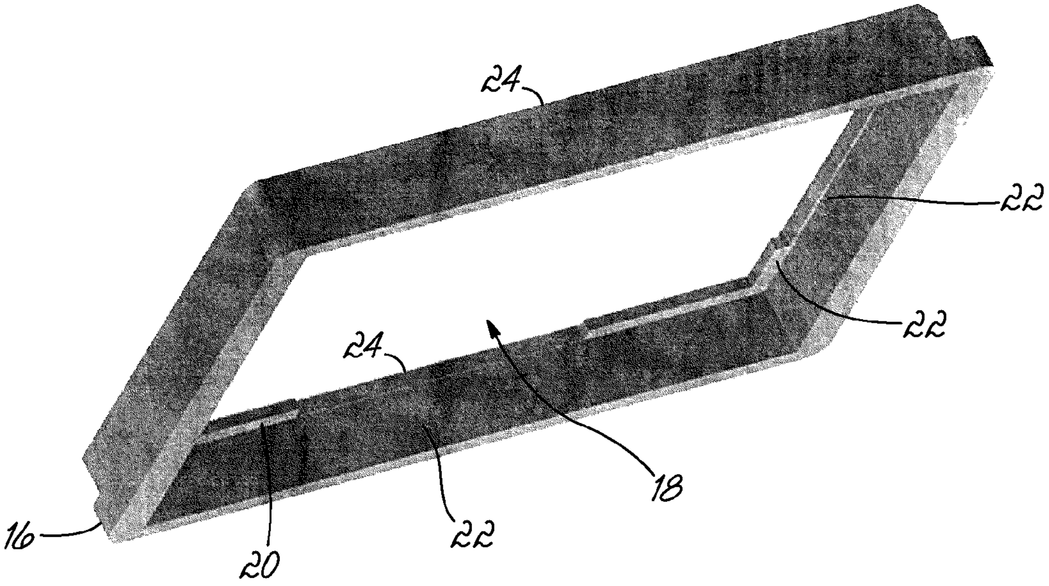
FIG. 1 is a perspective view of a frame component of a multiwell plate device according to one embodiment of the present invention.
Figure 2:
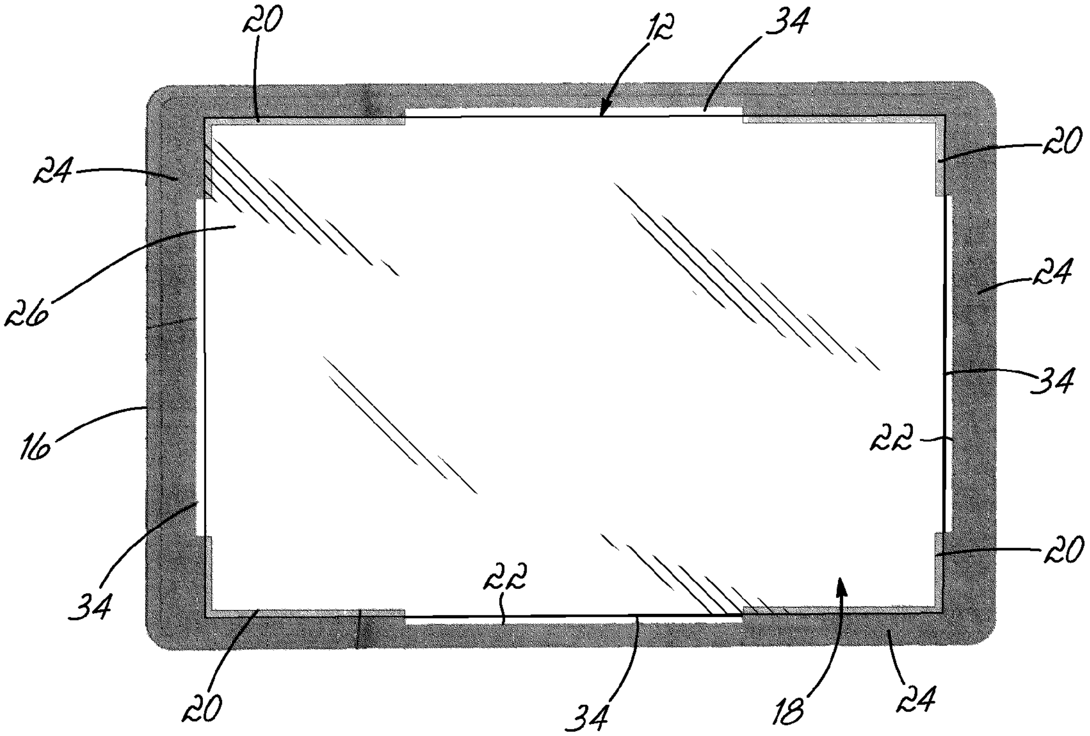
FIG. 2 is a top view of the frame with a transparent substrate in place.
Figure 3:
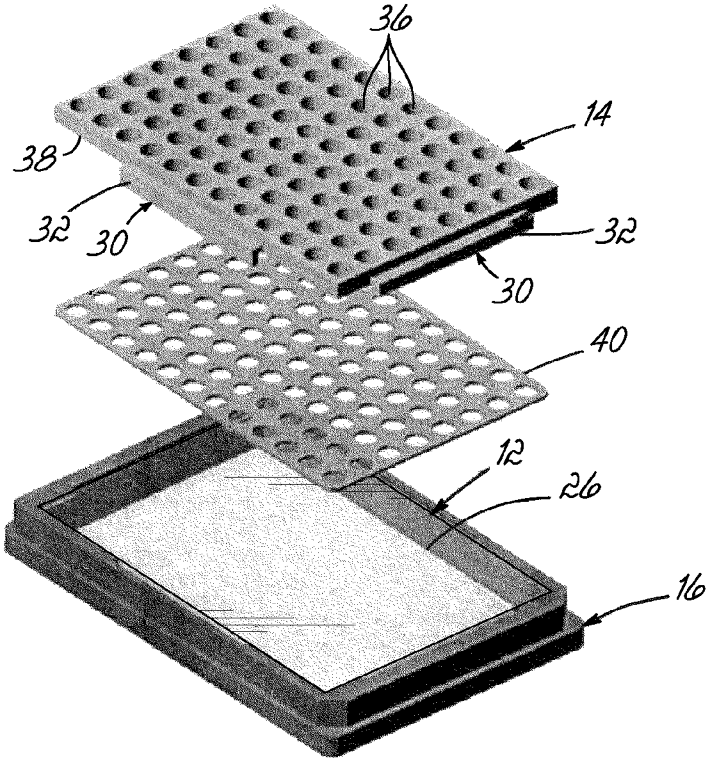
FIG. 3 is an exploded view of a multiwell structure, an adhesive carrier layer and the substrate contained in the frame prior to assembly.
Figure 4:
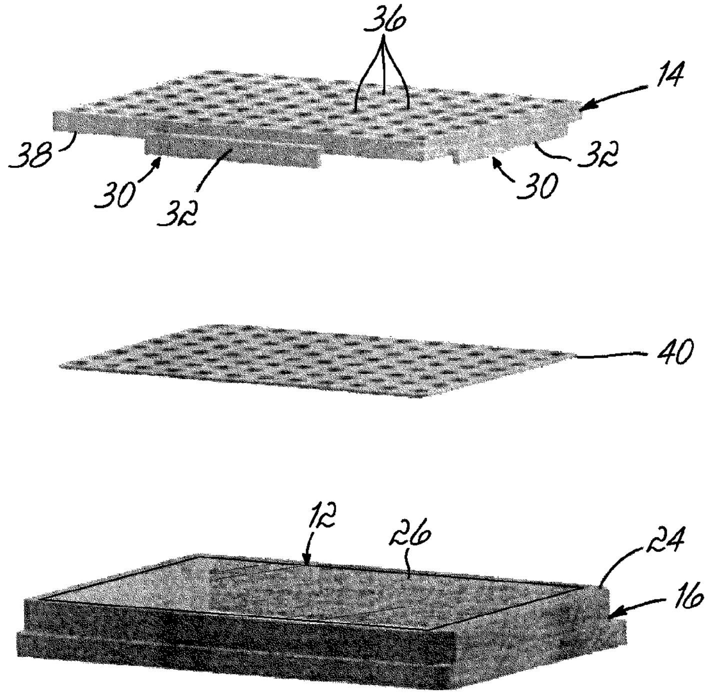
FIG. 4 is another view of the components shown in FIG. 3.
Figure 5:
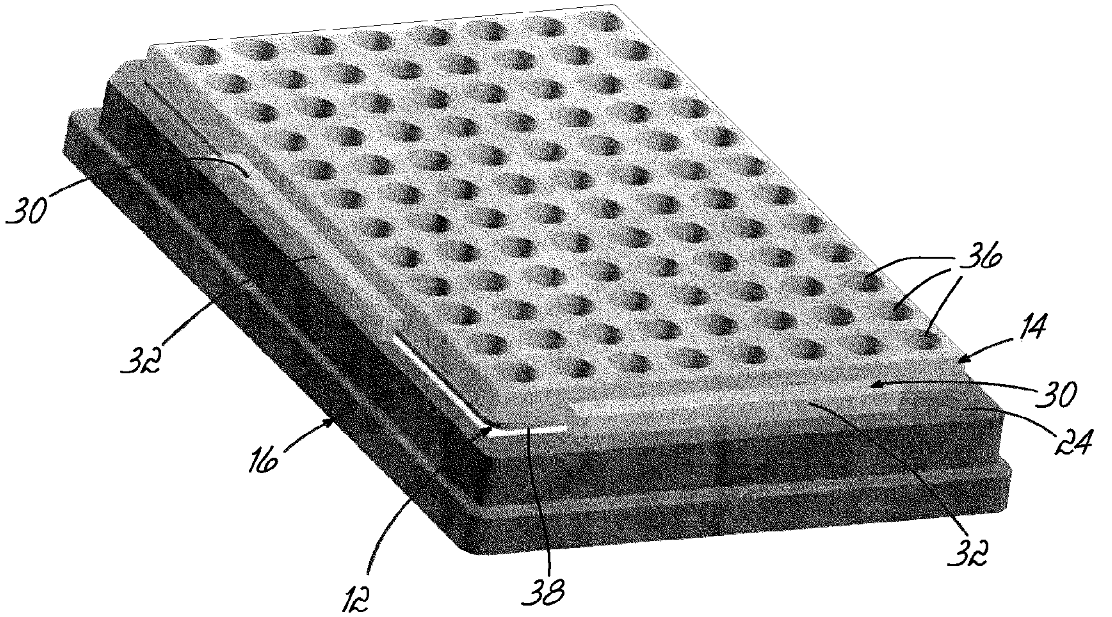
FIG. 5 is a perspective view of the multiwell structure attached to the substrate while contained within the frame.
Figure 6:
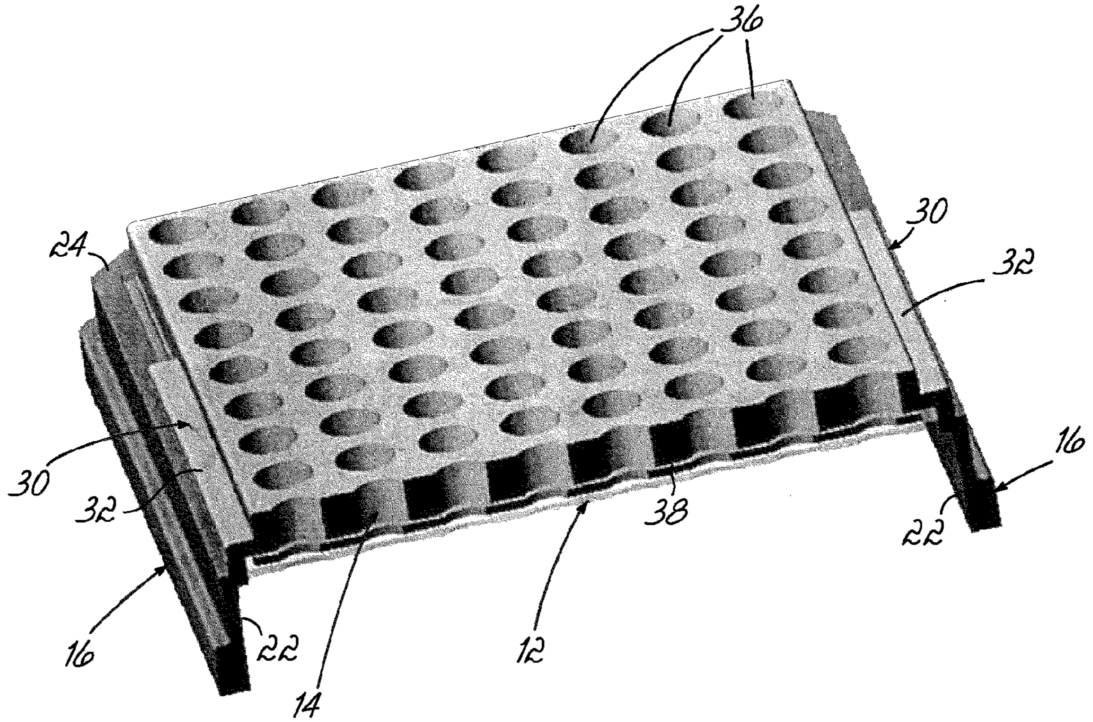
FIG. 6 is a cut-away view of the multiwell structure attached to the substrate while contained within the frame.

Referring to FIGS. 1 and 2, the frame 16 has an open area 18 used to contain the substrate 12 for processing in an automated array printer or other instrument or for manual processing. In a preferred embodiment, the frame 16 has a "footprint" that conforms to the standard dimensions for multiwell plates (SBS Standards), for example, 85.5×127.6 mm. The open area 18 in the frame 16 may vary depending upon the size of the substrate 12 but preferably should be sized so that it nearly matches the dimensions of the substrate 12 to prevent detrimental movement or shifting of the substrate 12 during processing. For example, if using a substrate 12 of about 75.7 mm×111.3 mm, an open area 18 of about 75.8 mm×111.4 mm is suitable.

The substrate 12 rests upon ledges 20 or other protrusions on the inner surfaces 22 of the frame 16. Preferably, the depth of the ledges 20 from a top surface 24 of the frame 16 is approximately equal to the thickness of the substrate 12 such that a reaction surface 26 of the substrate 12 as it sits in the open area 18 is essentially flush with the top surface 24 of the frame 16. For example, if the substrate 12 is 1 mm in thickness, the ledges 20 are preferably located about 1 mm below the top surface 24 of the frame 16.

Once the substrate 12 is in place in the open area 18 of the frame 16, an automated arrayer or instrument is used to print or spot arrays in a pattern that matches the SBS Standard pattern of wells, or any other desired pattern, without the need for wasted vertical movement typically needed when printing or spotting the bottom of a conventional multiwell plate.

Figure 9:
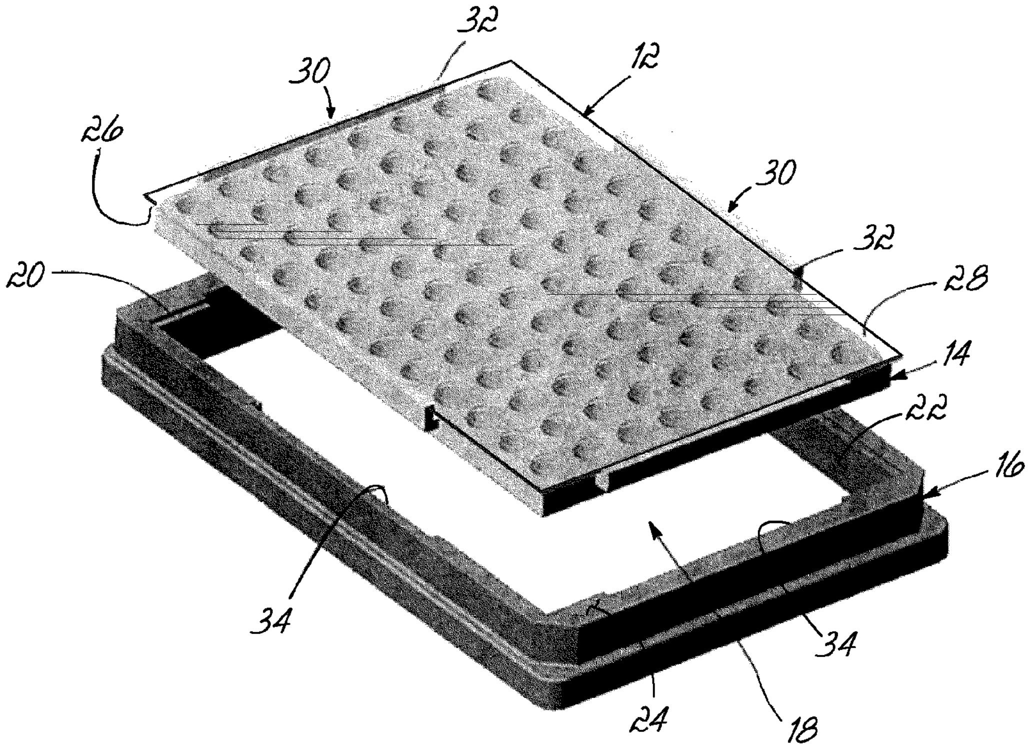
FIG. 9 shows the multiwell structure with attached substrate removed from the frame and inverted 180° for reinsertion into the frame.

Referring to FIGS. 3-6, after the substrate 12 is printed or spotted or otherwise processed, the bottomless multiwell structure 14 is attached to the reaction surface 26 of the substrate 12 while in place on the frame 16. Preferably, the dimensions of the multiwell structure 14 are smaller than those of the substrate 12 so that the substrate 12 forms a perimeter 28 (as shown in FIG. 9) around the multiwell structure 14. For example, if the substrate 12 is about 75.7 mm×11.3 mm, the multiwell structure 14 might be about 73 mm×108.6 mm.

In one embodiment, the multiwell structure 14 has two or more lateral projections 30 each with a downwardly extending portion serving as alignment tabs 32 that mate with alignment receptors 34 in the frame 16 to guide the placement of the multiwell structure 14 onto the substrate 12 so that the wells 36 of the multiwell structure 14 correspond with the printed or spotted areas of the substrate 12. The size, shape and number of the lateral projections 30, alignment tabs 32 and corresponding alignment receptors 34 may be varied as long as multiwell structure 14 can be placed onto the reaction surface 26 of the substrate 12 with sufficient accuracy in relation to the arrays or other material contained on the substrate 12.

In one embodiment, the surface 38 (see FIGS. 4 and 5) of the multiwell structure 14 that contacts the substrate 12 contains a pre-applied adhesive (not shown). A removable liner (not shown) may be used to protect the adhesive layer until time of use. In another embodiment, shown in FIGS. 3 and 4, a thin flat adhesive carrier layer 40 is used to attach the multiwell structure 14 to the substrate 12. For example, the carrier layer 40 has adhesive on both sides and forms an intervening layer between the multiwell structure 14 and the substrate 12. For convenience, the multiwell structure 14 can be supplied with the carrier layer 40 already attached to its surface 38.

When the alignment tabs 32 are inserted into the alignment receptors 34 in the frame 16, downward pressure may be applied to the multiwell structure 14 to affect a functional seal or attachment to the substrate 12.

Figure 7:
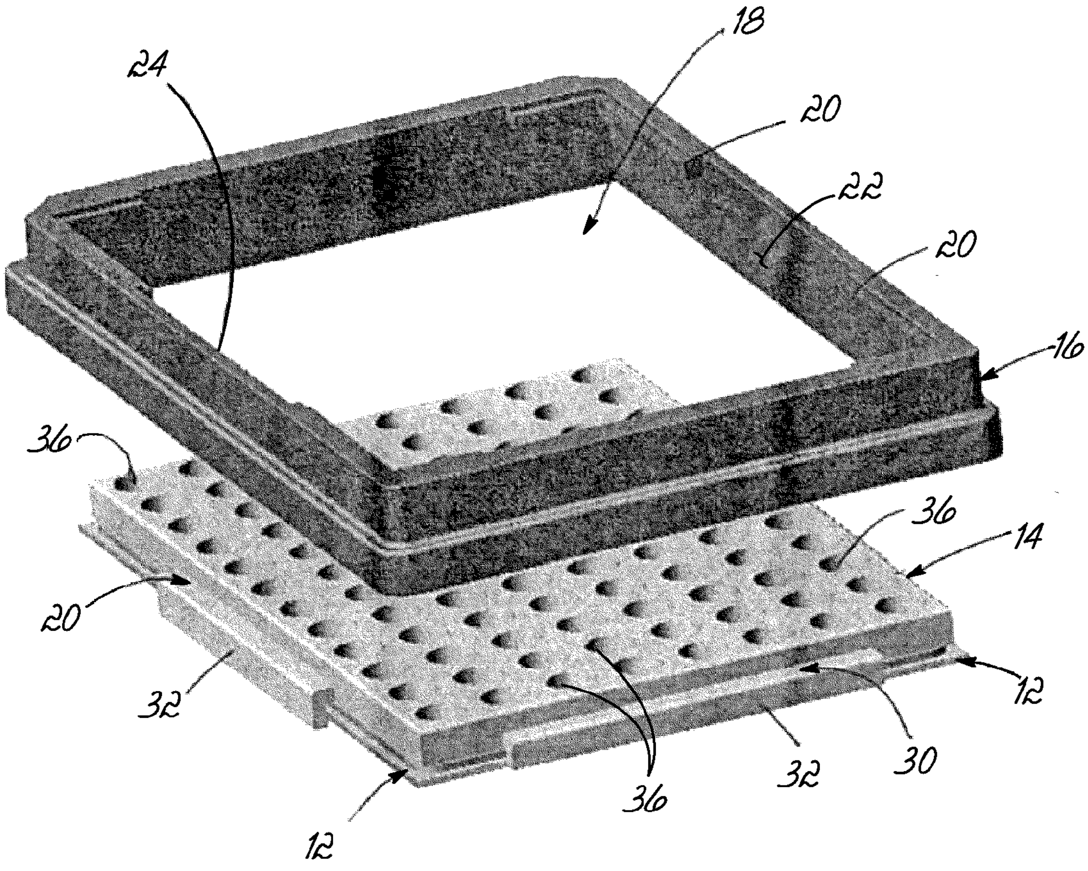
FIG. 7 is a view of the multiwell structure with attached substrate being positioned into the frame from below.
Figure 8:
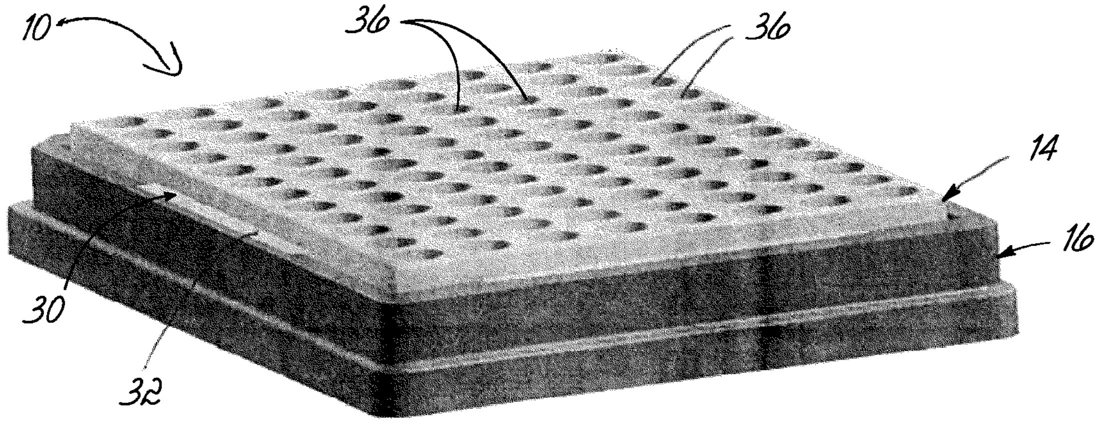
FIG. 8 is a perspective view of the assembled multiwell plate device.

Referring to FIGS. 7 and 8, after the multiwell structure 14 and substrate 12 are attached, they are lifted from the frame 16 and then reinserted from underneath the frame 16 with the open end of the wells 36 facing upward through the open area 18 in the frame 16. The lateral projections 30 of the multiwell structure 14 facilitate alignment by fitting into the alignment receptors 34 or other receptive features in the frame 16. The multiwell structure 14 with attached substrate 12 is pushed upward through the open area 18 of the frame 16 until the reaction surface 26 of the substrate 12 abuts the underside of the ledges 20 provided on the inner sidewall 22 of the frame 16.

In one embodiment, the multiwell structure 14 and/or the lateral projections 30 fit snugly to hold the multiwell structure 14 securely in the frame 16. Optionally, features on the internal sidewalls 22 of the frame 16 (not shown) may be used to secure or enhance the fit. The multiwell plate device 10 assembled in this mode can be used in substantially the same way as a conventional single-piece multiwell plate device.

For scanning or other analysis, the multiwell place device 10 may be used as shown in FIG. 8. Alternatively, the multiwell structure 14 with the substrate 12 attached may be removed from the frame 16 through application of manual force to the multiwell structure 14 and then inverted 180° so that the open ends of the wells 36 are facing down and the substrate 12 is on top, as shown in FIG. 9.

Figure 10:
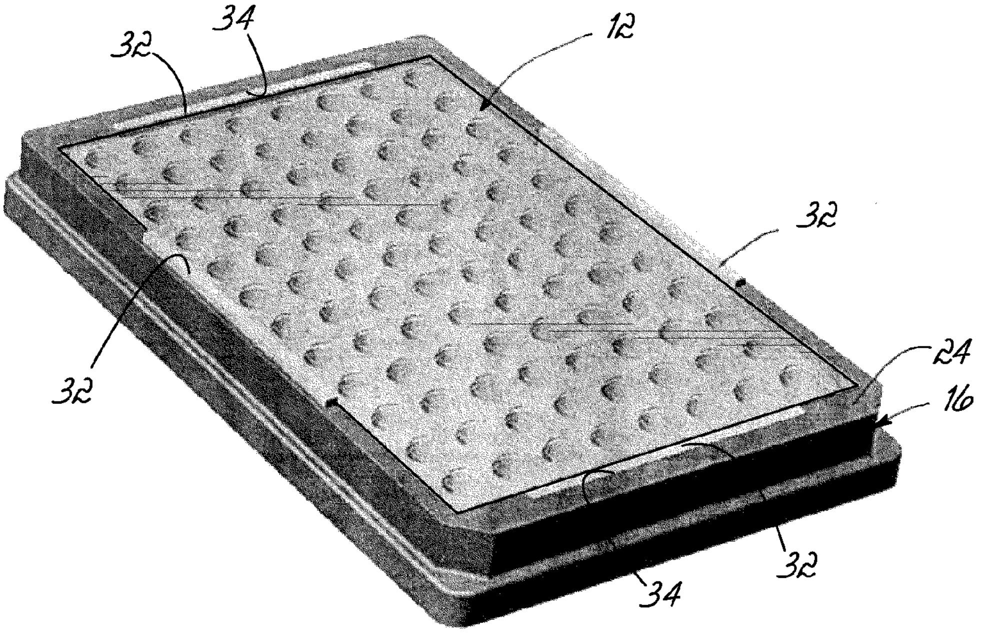
FIG. 10 is a perspective view of the inverted plate assembly.

Continuing with FIGS. 9 and 10, the multiwell structure 14 is inserted into the open area 18 in the frame 16 from above and lowered so that the substrate 12 comes to rest on the top surface of the ledges 20 provided on the inner sidewalls 22 of the frame 16. The reaction surface 26 of the substrate 12 is now at the level of the top surface of the ledges 20 whereas in the other format or "mode" (with the multiwell structure 14 facing up), the reaction surface 26 is at the level of the bottom surface of the ledges 20, thus the focal plane differs only by the thickness of the ledges 20. The thickness of the ledges 20 is generally influenced by the material used to form the frame 16 since the material strength of the ledges 20 must be sufficient to bear the weight of the multiwell structure 14 and substrate 12. Typically, a thickness of about 0.3-1.0 mm is adequate for most materials suitable for manufacturing the frame 16.

Now referring to an alternative embodiment of the present invention, a multiwell plate device 100 is shown in FIGS. 12-15 comprising at least three components: i) a substantially flat substrate 102, ii) a bottomless multiwell structure 104 and a frame 106. In another aspect, the invention is a method for scanning a reaction surface from above and/or below.

Figure 12:
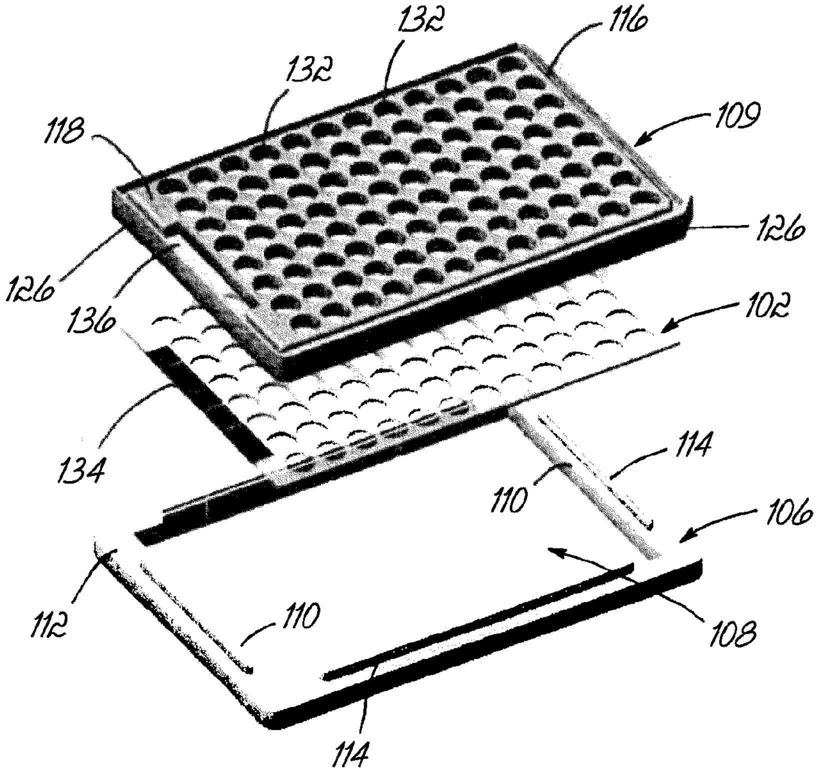
FIG. 12 is an exploded view of a multiwell structure, substrate and frame prior to assembly according to another embodiment of the present invention.

Referring to FIG. 12, the frame 106 has an open area 108 used to contain the substrate 102 for processing in an automated array printer or other instrument or for manual processing. In a preferred embodiment, the frame 106 has a "footprint" that conforms to the standard dimensions for multiwell plates (SBS Standards), for example, 85.5×127.6 mm. The open area 108 in the frame 106 may vary depending upon the size of the substrate 102 but preferably should be sized so that it nearly matches the dimensions of the substrate 102. For example, as shown in FIG. 12, if using a substrate 102 of about 75.7 mm×111.3 mm, an open area 108 of about 75.5 mm×111.1 mm permits the substrate 102 to rest upon a receiving surface 110 of the frame 106. In one embodiment, the receiving surface 110 is slightly elevated compared to the remaining outer surface 112 of the frame 106 as shown in FIG. 15.

To minimize movement of the substrate 102 while positioned on the frame 106, one or more ridges 114 or other protrusions may be included on the frame 106. FIG. 12 shows ridges 114 on each of the four sides of the frame 106, but variations are contemplated, including a continuous ridge surrounding the entire open area 108 or multiple ridges 114 on the same side or the ridges 114 may be limited to fewer than all four sides of the frame 106.

Figure 15:
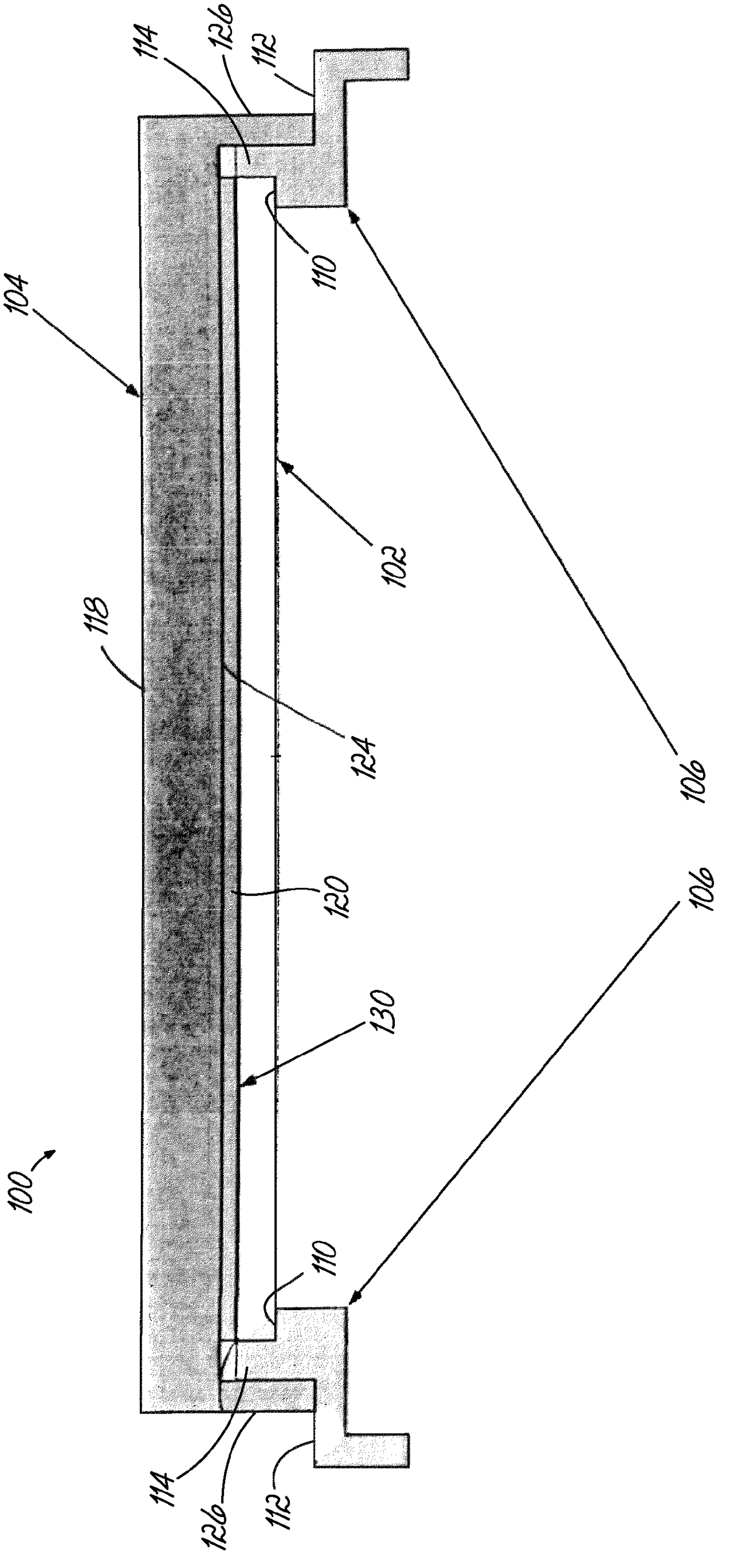
FIG. 15 is a cross-section of the assembled multiwell plate shown in FIG. 14.

In the embodiment shown in FIG. 15, the height of a ridge 114 is greater than the thickness of the substrate 102 such that the ridge 114 defines the receiving surface 110 for the substrate 102 adjacent the open area 108. For example, if the substrate 102 is 1 mm in thickness, the ridges 114 may be about 2.8 mm in height above the outer surface 112 of the frame 106. The receiving area 110 is elevated compared to the remaining outer surface 112 of the frame 106. The ridges 114 also permit the multiwell structure 104 to fit securely to the frame 106 without adhesive contact between the multiwell structure 104 and the frame 106. Further, the ridges 114 mate with one or more grooves 116 in the top surface 118 of the multiwell structure 104 when the structure 104 with attached substrate 102 is used in an inverted format.

For additional ease in assembling the device, optional structural features may be included on the substrate 102 and/or the frame 106 that permit the substrate 102 to fit into the frame 106 in only one orientation. For example, a corner of the substrate 102 and a corresponding corner of the frame 106 may be angled or notched to permit a matched fit (not shown). Alternative means of dictating orientation are contemplated.

Once the substrate 102 is in place in the open area 108 of the frame 106, and optionally before the multiwell structure 104 is placed onto the substrate 102, an automated arrayer or instrument is used to print or spot arrays in a pattern that matches the SBS Standard pattern of wells, or any other desired pattern (not shown). The positioning of the substrate 102 in the frame 106 also serves to properly locate the substrate 102 relative to the X, Y stops which are standard on arrayer platforms (not shown).

After the substrate 102 is printed or spotted or otherwise processed, the bottomless multiwell structure 104 is attached to a reaction surface 120 of the substrate 102 while in place on the frame 106. In the embodiment shown in FIGS. 12-15, the dimensions of the multiwell structure 104 are greater than those of the substrate 102 so that the multiwell structure 104 fits over the ridges 114 on the frame 106.

Figure 13:
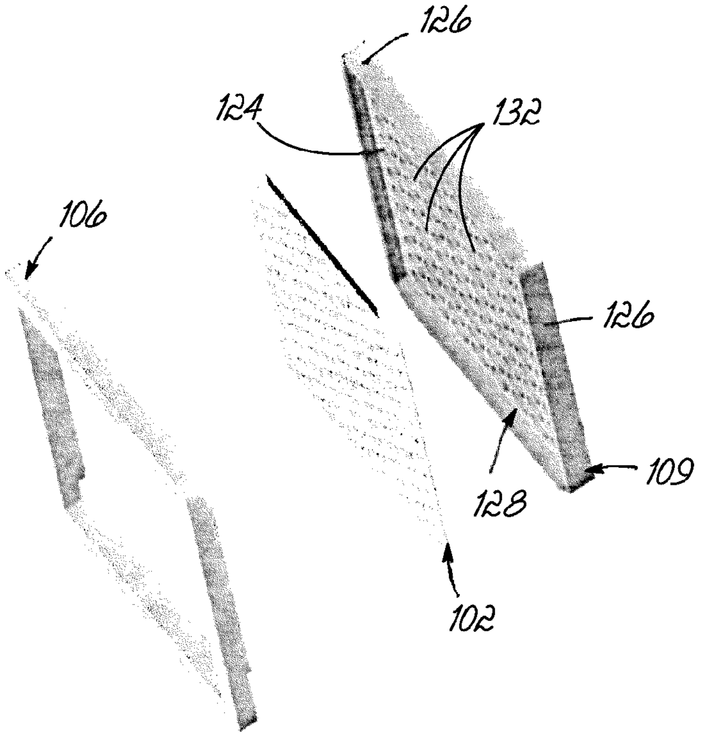
FIG. 13 is a further exploded view of the multiwell structure, substrate and frame shown in FIG. 12 prior to assembly.

As shown in FIGS. 12, 13 and 15, the multiwell structure 104 has the top surface 118, a bottom surface 124 and four sidewalls 126. The bottom surface 124 provides the surface for attachment to the reaction surface 120 of the substrate 102. Since the sidewalls 126 fit flush against the frame 106 when assembled, a recessed area or "pocket" 128 is provided in the bottom surface 124 to accommodate the thickness of the substrate 102. For example, if the substrate 102 is about 1 mm in thickness, the pocket 128 is at least 1 mm in depth to provide additional allowance for adhesive, so that the bottom surface 124 of the multiwell structure 104 makes full contact with the substrate 102 via an intervening adhesive layer 130 when assembled. The ridges 114 may serve as alignment guides for the multiwell structure 104 to guide the placement of the multiwell structure 104 onto the substrate 102 so that the wells 132 of the multiwell structure 104 correspond with the printed/spotted areas of the substrate 102.

In one embodiment, the bottom surface 124 of the multiwell structure 104 that contacts the substrate 102 contains a pre-applied adhesive (not shown). A removable liner (not shown) may be used to protect the adhesive layer until time of use. Alternatively, a thin flat adhesive carrier layer (not shown) is used to attach the multiwell structure 104 to the substrate 102. For example, the carrier layer has adhesive on both sides and forms an intervening layer between the multiwell structure 104 and the substrate 102. For convenience, the multiwell structure 104 can be supplied with the carrier layer already attached to its bottom surface 124.

Figure 14:
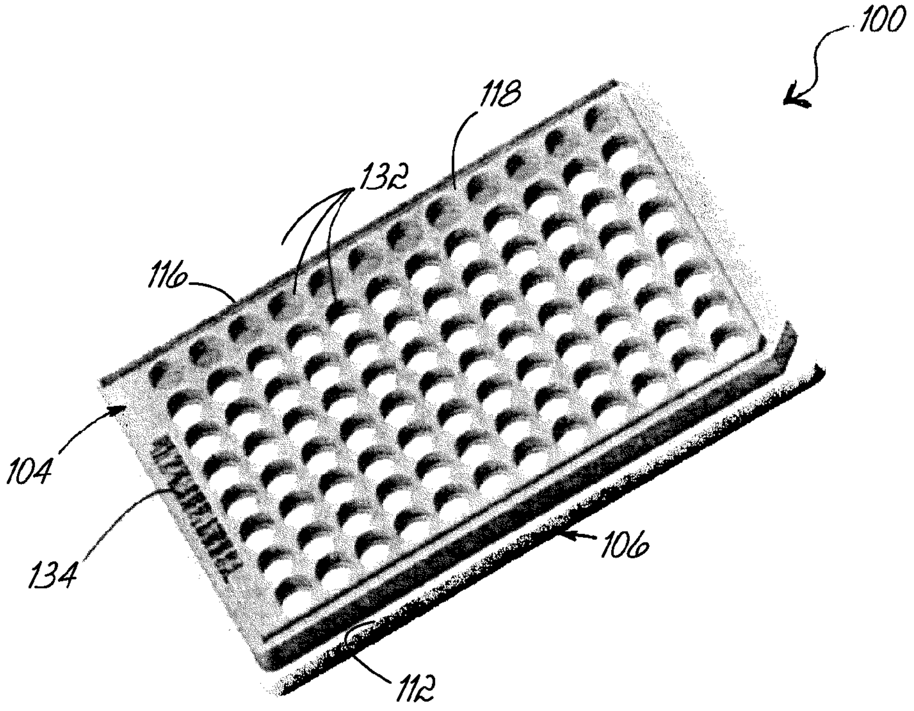
FIG. 14 is a perspective view of the assembled multiwell plate of FIGS. 12 and 13.

When the ridges 114 are inserted into the pocket 128 in the bottom surface 124 of the multiwell structure 104, downward pressure may be applied to the multiwell structure 104 to affect a functional seal or attachment to the substrate 102 via the adhesive 130, as shown in FIG. 15. FIG. 14 shows the fully assembled plate device 100. The multiwell plate device 100 assembled in this mode can be used in substantially the same way as a conventional single-piece multiwell place device.

Alternatively, the multiwell structure 104 with the substrate 102 attached may be removed from the frame 106 through application of manual force to the multiwell structure 104 and then inverted 180° so that the open ends of the wells 132 are facing downward and the substrate 102 is on top. The multiwell structure 104 may then be attached to the frame 106 by aligning the ridges 114 on the frame 106 with the grooves 116 in the top surface 122 of the multiwell structure 104 so that the sidewalls 126 are flush against the frame 106.

With regards to manufacture, the substrates 12, 102 may be made from any substantially flat material useful for containing biological materials. In a preferred embodiment, the substrate is glass, but alternatively, silicon, quartz, plastics, metals or other materials may be used. Further, part or all of the substrates 12, 102 may be treated and/or coated with other chemicals or compounds to enhance qualities including, without limitation, binding capacity or specificity, as is known in the art, or the substrates 12, 102 may be uncoated/untreated. Also, the substrates 12, 102 may be transparent, translucent or opaque or any combination of the above. While the present invention has been exemplified as having a single substrate 12, 102, multiple smaller substrates may be utilized (not shown). For example, multiple glass microscope slides could be substituted for a single substrate. Further, the thickness of the substrates 12, 102 can be varied. Typically, a substrate 12, 102 with a thickness in the range of 0.3 mm-1.0 mm is suitable for many uses but the thickness can be increased or decreased.

An optional feature of the substrate 102 is a bar code or other indicia 134 (see FIGS. 12 and 14) to facilitate identification, inventory, tracking, processing and/or other aspects of the handling of the substrate 102 and/or assembled multiwell plate 100. To facilitate viewing of the indicia 134 an aperture or window 136 (see FIG. 12) may be provided in the multiwell structure 104 or frame 106.

Figure 11:
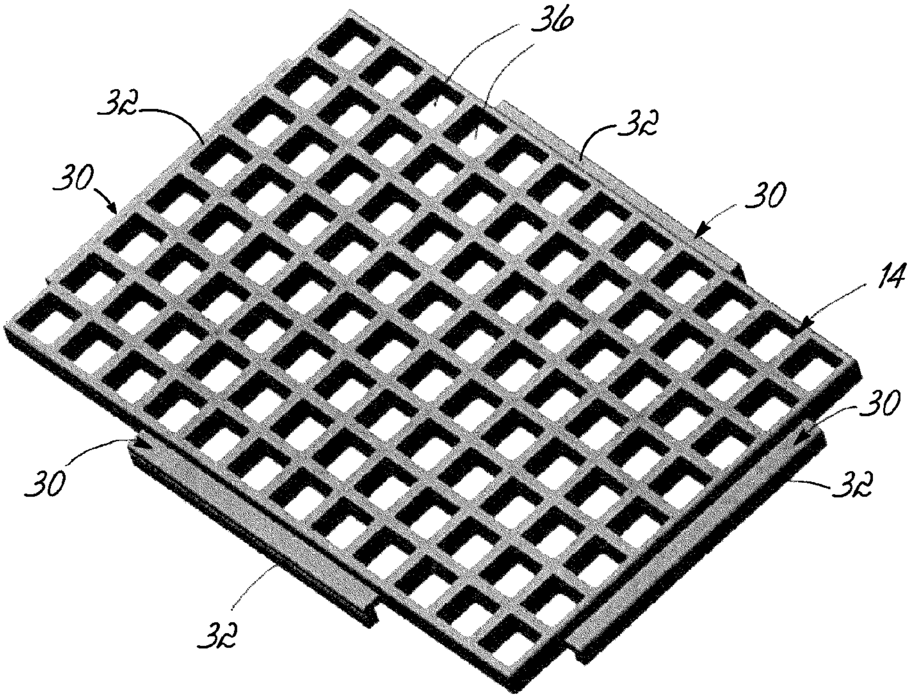
FIG. 11 is a perspective view of an alternative multiwell structure having square wells.

The multiwell structures 14, 104 can be made from any moldable material, such as a plastic polymer, and may be rigid or flexible. Material cost may be a factor because the multiwell structures 14, 104 are ideally disposable after use. By way of non-limiting example, polystyrene, polypropylene and the like provide suitable materials for the multiwell structures 14, 104. Dimensions of the multiwell structures 14, 104 may vary depending upon the width and length of the substrates 12, 102 or composite of multiple substrates. Further, the wells 36, 132 of the multiwell structures 14, 104 should be formatted to meet SBS Standards. The depth of the wells 36, 132 may conform to SBS Standards or alternatively, shallow depths are suitable. In one embodiment, the depth of the wells 36, 132 in the multiwell structures 14, 104 is no more than 5 mm (more shallow than SBS Standards). Further, the shape of the wells 36, 132 may be round as shown in FIGS. 3-10 and 12-14 or they may be some other shape such as square-shaped as shown in FIG. 11.

The frames 16, 106 are molded or machined from any number of materials including, without limitation, plastic polymers, acrylics and metals. The frames 16, 106 may be disposable or reusable depending upon the durability of the material used, cost, etc. The height of the frames 16, 106 may conform to SBS Standards or it can be varied according to the depth of the multiwell structures 14, 104. For example, if the multiwell structures 14, 104 are about 4-5 mm in depth, an appropriate height for the frame 16 is about 13.5-14.0 mm and the appropriate height for the frame 106 is about 5.0-14.0 mm.

The optional adhesive carrier layer 40 may comprise a film or resilient gasket-like material such as silicone or closed-cell polyethylene foam and the like. Preferably the adhesive used to attach the substrates 12, 102 to the multiwell structures 14, 104 is irreversible but alternatively, a reversible adhesive may be more appropriate for certain uses. Likewise, a combination of irreversible adhesive on one side of the carrier layer 40 and reversible adhesive on the other side may be used. Adhesives of these types are known in the art.

Other embodiments of the invention may be apparent to those skilled in the art and are considered to be part of the scope and spirit of the present invention. The descriptions and examples provided herein are intended to be exemplary and not limiting with regards to the scope of the invention.

While the present invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method and illustrative examples shown and described. Accordingly, departures may be made from such details without departing from the scope or spirit of Applicants' general inventive concept.

Having described the invention, we claim:

1. A multiwell plate device, comprising:

a frame having a top surface and defining an opening therethrough with said frame being disposed in a predetermined orientation;

a substrate engaging member disposed adjacent at least a portion of the opening and having a top surface and an opposite bottom surface, each of the top surface and bottom surface of said substrate engaging member being located below the top surface of said frame;

a substrate having a reaction surface and an opposite bottom surface and being configured to engage the substrate engaging member and;

a multiwell structure supported by said substrate and having a plurality of bottomless wells formed therein, wherein in an upright orientation of said substrate and said multiwell structure with said multiwell structure located above said substrate, said multiwell structure and said substrate are inserted into the opening from beneath said frame, with said frame disposed in the predetermined orientation, with said reaction surface of said substrate engaging the bottom surface of said substrate engaging member, and further wherein in an inverted orientation of said substrate and said multiwell structure with said multiwell structure located beneath said substrate, said multiwell structure and said substrate are inserted into the opening from above said frame, with said frame disposed in the predetermined orientation, with said reaction surface of said substrate engaging the top surface of said substrate engaging member.

2. The multiwell plate device of claim 1, wherein said substrate engaging member comprises a ledge at least partially surrounding the opening.

3. The multiwell plate device of claim 1, wherein the top surface of said substrate engaging member is located below the top surface of said frame by a depth substantially equal to a thickness of said substrate.

4. The multiwell plate device of claim 3, wherein in the inverted orientation of said substrate and said multiwell structure, the bottom surface of said substrate is generally flush with the top surface of said frame.

5. The multiwell plate device of claim 1, further comprising cooperating first and second alignment structure provided on said multiwell structure and said frame, respectively, to align said multiwell structure relative to said frame while said multiwell structure and said substrate are inserted into the opening from above and beneath said frame.

6. The multiwell plate device of claim 5, wherein said first alignment structure provided on said multiwell structure comprises at least one lateral projection.

7. The multiwell plate device of claim 6, wherein said first alignment structure further comprises an alignment tab depending from said at least one lateral projection.

8. The multiwell plate device of claim 6, wherein said second alignment structure provided on said frame comprises at least one notch configured to receive said at least one lateral tab of said first alignment structure.

9. The multiwell plate device of claim 1, further comprising an adhesive layer disposed between the reaction surface of said substrate and said multiwell structure.

10. A method of using a multiwell plate device including a frame having a top surface and defining an opening therethrough with the frame being disposed in a predetermined orientation, a substrate engaging member disposed adjacent at least a portion of the opening and having a top surface and an opposite bottom surface, each of the top surface and bottom surface of the substrate engaging member being located below the top surface of the frame, a substrate having a reaction surface and an opposite bottom surface and being configured to engage the substrate engaging member, and a multiwell structure supported by said substrate and having a plurality of bottomless wells formed therein, comprising:

in an upright orientation of the substrate and the multiwell structure with the multiwell structure located above the substrate, inserting the multiwell structure and the substrate into the opening from beneath the frame, with the frame disposed in the predetermined orientation, with the reaction surface of the substrate engaging the bottom surface of the substrate engaging member; and in an inverted orientation of the substrate and the multiwell structure with the multiwell structure located beneath the substrate, inserting the multiwell structure and the substrate into the opening from above the frame, with the frame disposed in the predetermined orientation, with the reaction surface of the substrate engaging the top surface of the substrate engaging member.

11. The method of claim 10, wherein in the inverted orientation of the substrate and the multiwell structure, the bottom surface of the substrate is generally flush with the top surface of the frame.

12. The method of claim 10, further comprising the step of engaging the multiwell structure with the reaction surface of the substrate using an adhesive.

13. The method of claim 10, further comprising the step of aligning the multiwell structure relative to the frame while the multiwell structure and the substrate are inserted into the opening from above and beneath the frame.

14. A multiwell plate device, comprising:

a frame defining an opening therethrough, a substrate receiving surface disposed adjacent at least a portion of the opening;

a substrate having a reaction surface and an opposite bottom surface and being configured to engage the substrate receiving surface;

a multiwell structure supported by said substrate and having a plurality of bottomless wells formed therein, said multiwell structure having a pocket formed on a lower side thereof for receiving said substrate therein with said reaction surface engaging said multiwell structure and at least one recess formed in an opposite upper side thereof; and at least one projection extending upwardly from said frame and positioned outwardly of said substrate receiving surface so as to define the substrate receiving surface and being configured to register said substrate relative to said frame;

wherein in an upright orientation of said substrate and said multiwell structure with said multiwell structure located above said substrate, the bottom surface of said substrate engages said substrate receiving surface with said substrate received within said pocket, and further wherein in an inverted orientation of said substrate and said multiwell structure with said multiwell structure located beneath said substrate, said at least one projection is received within said at least one recess formed in the upper side of said multiwell structure.

15. The multiwell plate device of claim 14, further comprising an adhesive layer disposed between the reaction surface of said substrate and said multiwell structure.

16. The multiwell plate device of claim 14, wherein said at least one projection comprises an elongated ridge.

17. The multiwell plate device of claim 14, wherein said at least one recess comprises a groove.

18. The multiwell plate device of claim 14, further comprising indicia provided on said substrate.

19. The multiwell plate device of claim 18, further comprising a window provided on said multiwell structure.

20. A method of using a multiwell plate device including a frame defining an opening therethrough, a substrate receiving surface disposed adjacent at least a portion of the opening, a substrate having a reaction surface and an opposite bottom surface and being configured to engage the substrate receiving surface, a multiwell structure supported by said substrate and having a plurality of bottomless wells formed therein, a pocket formed on a lower side thereof and at least one recess formed in an opposite upper side thereof, and a projection extending upwardly from the frame and positioned outwardly of the substrate receiving surface so as to define the substrate receiving surface and being configured to register the substrate relative to the frame, comprising:

in an upright orientation of the substrate and the multiwell structure with the multiwell structure located above the substrate, engaging the bottom surface of the substrate with the substrate receiving surface while receiving the substrate within the pocket; and in an inverted orientation of the substrate and the multiwell structure with the multiwell structure located beneath the substrate, receiving the at least one projection within the at least one recess formed in the upper side of the multiwell structure.

21. The method of claim 20, further comprising the step of engaging the multiwell structure with the reaction surface of the substrate using an adhesive.

22. A multiwell plate device, comprising:

a frame having a top surface and defining an opening therethrough with said frame being disposed in a predetermined orientation;

a substrate engaging member disposed adjacent at least a portion of the opening and having a top surface and an opposite bottom surface, each of the top surface and bottom surface of said substrate engaging member being located below the top surface of said frame;

a substrate having a reaction surface and an opposite bottom surface and being configured to engage the substrate engaging member and;

a multiwell structure supported by said substrate and having a plurality of bottomless wells formed therein, wherein in an upright orientation of said substrate and said multiwell structure with said multiwell structure located above said substrate, said multiwell structure and said substrate are inserted into the opening from beneath said frame, with said frame disposed in the predetermined orientation, with said reaction surface of said substrate being located beneath said substrate engaging member, and further wherein in an inverted orientation of said substrate and said multiwell structure with said multiwell structure located beneath said substrate, said multiwell structure and said substrate are inserted into the opening from above said frame, with said frame disposed in the predetermined orientation, with said reaction surface of said substrate being located above said substrate engaging member.

23. The multiwell plate device of claim 22, wherein said substrate engaging member comprises a ledge at least partially surrounding the opening.

24. The multiwell plate device of claim 22, wherein in the inverted orientation of said substrate and said multiwell structure, the bottom surface of said substrate is generally flush with the top surface of said frame.

25. The multiwell plate device of claim 22, further comprising cooperating first and second alignment structure provided on said multiwell structure and said frame, respectively, to align said multiwell structure relative to said frame while said multiwell structure and said substrate are inserted into the opening from above and beneath said frame.

26. The multiwell plate device of claim 25, wherein said first alignment structure provided on said multiwell structure comprises at least one lateral projection.

27. The multiwell plate device of claim 26, wherein said first alignment structure further comprises an alignment tab depending from said at least one lateral projection.

28. The multiwell plate device of claim 26, wherein said second alignment structure provided on said frame comprises at least one notch configured to receive said at least one lateral tab of said first alignment structure.

29. The multiwell plate device of claim 22, further comprising an adhesive layer disposed between the reaction surface of said substrate and said multiwell structure.

* * * * *